US00PP17682P2

(12) United States Plant Patent
Abrahamson et al.

(10) Patent No.: US PP17,682 P2
(45) Date of Patent: May 1, 2007

(54) FAST-GROWING WILLOW SHRUB NAMED 'ONEIDA'

(50) Latin Name: ***Salix purpurea*×*S. miyabeana***
Varietal Denomination: Oneida

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/244,975

(22) Filed: Oct. 6, 2005

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
(74) *Attorney, Agent, or Firm*—Wall Marjama & Bilinski LLP

(57) ABSTRACT

A distinct male cultivar of *Salix purpurea*×*S. miyabeana* named 'Oneida', characterized by rapid stem growth producing 2.7-times greater woody biomass than one of its parents ('SX67') and greater than 36% more biomass than current production cultivars ('SV1' and 'SX64'). 'Oneida' can be planted from dormant stem cuttings, produces multiple stems after coppice, and the stem biomass can be harvested when the plant is dormant. In the spring following harvest, the plant will re-sprout very vigorously, producing new stems that can be harvested after two to four years of growth. This harvest cycle can be repeated several times. The stem biomass can be chipped and burned as a source of renewable energy, generating heat and/or electricity. 'Oneida' displays a low incidence of rust disease or damage by beetles or sawflies.

11 Drawing Sheets

STATEMENT AS TO RIGHTS TO INVENTIONS MADE UNDER FEDERALLY-SPONSORED RESEARCH AND DEVELOPMENT

The invention described herein was reduced to practice during the funding period of Contract 4000003235 (SUNY Research Foundation Award 011275) awarded by Oak Ridge National Laboratory, managed by UT-Batelle for the United States Department of Energy under contract DE-AC05-00OR22725, and of agreement number 6267 (SUNY Research Foundation Award 011536) awarded by the New York State Energy Research and Development Authority.

CROSS-REFERENCE TO RELATED APPLICATIONS

This application is related to the following plant patent applications, all of which are subject to assignment to the Research Foundation of the State University of New York, and each of which is being filed on even date herewith: "Fast-Growing Shrub Willow" Named 'Fish Creek', application Ser. No. 11/244,988; "Fast-Growing Shrub Willow" Named 'Canastota', application Ser. No. 11/244,986 +1; "Fast-Growing Shrub Willow" Named 'Millbrook', application Ser. No. 11/244,636; "Fast-Growing Shrub Willow" Named 'Otisco', application Ser. No. 11/244,987 "Fast-Growing Shrub Willow" Named 'Owasco', application Ser. No. 11/244,842 and "Fast-Growing Shrub Willow" Named 'Tully Champion', application Ser. No. 11/244,635 . The variety of fast-growing shrub willow named 'Oneida' was produced in the same willow breeding as were other varieties, including: 'Fish Creek', 'Canastota', 'Millbrook', 'Otisco', 'Owasco', and 'Tully Champion'.

BACKGROUND OF THE INVENTION

1. Field of the Invention

The invention is a new and distinct cultivar known by the varietal name 'Oneida' resulting from the novel hybridization of *Salix purpurea* with *Salix miyabeana*. The new variety was produced through controlled willow breeding conducted by the inventors in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing. Shrub willow is being developed as an agricultural crop plant that will be grown and harvested as a sustainable, renewable source of energy. Once a field planting of shrub willows is established, the woody stems can be harvested every three years, and new shoots will re-sprout the following season. Repeated harvesting every two to four years can be sustained for at least 15 years.

2. Description of Relevant Prior Art Including Information Disclosed Under 37 CFR 1.97–1.99

This new variety of ×*S. miyabeana* was the seedling progeny of the controlled pollination of the female clone *Salix purpurea* '94006' by the male clone *Salix miyabeana* 'SX67' performed in February 1999 in Syracuse, N.Y. The female plant (*Salix purpurea* '94006') has opposite leaves that are oblong or slightly obovate, apex obtuse or very shortly acuminate at the tip, entire margins and 2.0–2.3 cm in width. The variety 'Oneida' has alternate leaves that are obanceolate, apex tapering long-acuminate, with serrate margins and 1.0–1.3 cm in width. The plant has been propagated repeatedly by stem cuttings and has been found to retain its distinctive characteristics through successive propagations and field trails. More particularly, the plant has been asexually reproduced by collecting dormant stems during the winter months, cutting them into either 5 inch of 10 inch pieces (cuttings), then planting those cuttings in the field in the spring or in potting mix in the greenhouse, then transplanting the rooted cuttings to the field.

The female parent (*Salix purpurea* '94006') was originally identified in growing on the shore of a creek in Oneida County, N.Y., and was vegetatively propagated from stem cuttings. The male parent (*Salix miyabeana* 'SX67') was originally transferred from Toronto, Ontario, Canada, in 1994 and was vegetatively propagated in Syracuse, N.Y. from stem cuttings. The growth of the parent plants was characterized in experimental studies in Tully, N.Y. Both parents displayed rapid stem growth and low incidence of rust disease, so were chosen to serve as parents in a cross (identification #9980). The seedlings produced by this cross were first established in a greenhouse, and then were transplanted to a field in Syracuse, N.Y. This particular individual (identification #9980-005) was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normal daily minimum temperature in January of 14° F., and average precipitation of 40 inches. The new cultivar grows from a rooted cutting to a fully mature plant ready for harvest in approximately three years.

SUMMARY OF THE INVENTION

The *Salix purpurea*×*S. miyabeana* cultivar 'Oneida' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Oneida'. These characteristics in combination distinguish 'Oneida' as a new and distinct cultivar:

1. Rapid growth rate, producing 2.7-fold more woody biomass than one of its parents (*Salix miyabeana* 'SX67'), 45% more biomass than cultivar *Salix miyabeana* 'SX64', and 36% more biomass than a standard production cultivar, *Salix dasyclados* 'SV1' when grown in the same field for the same length of time (two growing seasons after coppice) in Tully, N.Y.
2. Low incidence of rust disease or mammal browse damage assessed in experimental trials in Syracuse, N.Y. in 2000.

BRIEF DESCRIPTION OF THE DRAWING

The accompanying color photographs show the features of the claimed cultivar in a manner as true as is reasonably possible. The illustrations include:

FIG. 1.1 illustrates two-year-old portion of stem collected while dormant;

FIG. 1.2 illustrates one-year-old portion of stem collected while dormant;

FIG. 1.3 illustrates a vegetative bud in dormancy;

FIG. 1.4 illustrates a floral bud in dormancy;

FIG. 1.5 illustrates new shoot growth from a stem cutting rooted in soil:sand in a greenhouse;

FIG. 1.6 illustrates upper leaf surface;

FIG. 1.7 illustrates lower leaf surface;

FIG. 1.8 illustrates mature catkin;

FIG. 1.9 illustrates stamen and densely pubescent floral bract;

FIG. 1.10 illustrates double vegetative buds; and

FIG. 2.1 illustrates stem biomass yield two years after coppice for the claimed cultivar as compared to other shrub willows.

DETAILED DESCRIPTION OF THE NEW PLANT

The following detailed description sets forth characteristics of the new plant. The following observations and measurements describe plants grown by asexual reproduction in Syracuse, N.Y. or Tully, N.Y. under conditions as described hereinabove. Color references are made using The Royal Horticultural Society Colour Chart (hereinafter The R.H.S. Colour Chart) of The Royal Horticultural Society of London, England, except where general terms of ordinary dictionary significance are used.

BOTANICAL DESCRIPTION OF THE PLANT

The following detailed description of the 'Oneida' variety is based on observations from 10 inch cuttings grown in a greenhouse in Syracuse, N.Y. Cuttings were grown in 7 inch tubes in a (1:1) ProMix®/sand (v/v) substrate under natural light from December 2004 to March 2005. Plants were irrigated with automatic misting for 6 minutes every 2 hours five times each day.

Latin name: *Salix purpurea*×*S. miyabeana.*
Varietal denomination: 'Oneida'.
Parentage:
*Female or seed parent.*—*S. purpurea* '94006'.
*Male or pollen parent.*—*S. miyabeana* 'SX67'.
Propagation:
*Type.*—Stem cutting.
*Time to rooting.*—Approximately 10 days in water at 21° C.
Precocity: Subprecocious — Catkins mature as leaves begin to break bud.
Plant description: The color of one-year-old stems observed when dormant are grey orange (RHS 171A), while two to three-year-old stems are yellow-green to pale green (RHS 152C, RHS 147C), bark cracking and cuticle slightly broken vertically. Additionally, the average diameter of the trunk (two-year old stems) at a height of 1 m above the ground is 1.7 cm. The bark color of field grown stems is yellow-green (#152B). The surface is fairly smooth with shallow thin longitudinal furrows and raised reddish lenticels. Vegetative buds are dark red (RHS 60A), typically 3.5 mm in length, and lingulate, occasionally occurring together as double buds. Lenticels are wart-like, randomly scattered, and red to yellow. The leaves are simple and alternate with pinnate venation. Petioles are typically 5 mm in length and yellow-green (#44B). Average pistils are 3 mm in length. Stipules are typically 5 mm in length, lanceolate, serrulate, and yellow-green (144D).

Pubescent immature leaves. Mature leaves are oblanceolate, acute apex, acute to obtuse base, typically 8.1–11.5 cm in length, 1.0–1.3 cm in width, serrulate margin, adaxial (upper) surface green (RHS 144A), abaxial (lower) surface light pale green (RHS 139C), and stem light pale green (RHS 145C), at five weeks of growth. The upper surface of the leaves is glabrous and glossy with distinct venation. The lower surface is glabrous and slightly glaucous.

The average plant height of a mature plant after three seasons of growth is 5–6 m, with a typical spread at the crown of 1.0–1.5 m when grown in the typical planting spacing of 0.6 m×0.7 m.

Flowering description: Dormant floral buds are elongated, ovoid, acute, abaxial surface rounded, adaxial surface flat, typically 11 mm in length, raised forming an acute angle with the stem, turned, and dark brown. Peduncle of catkin is short and bears 3 to 4 leafy bracts. Catkins are erect, approximately 3.3 mm in length, and densely flowered. Flowers have one stamen, one nectary, a densely pubescent floral bract with a pink-purple acute apex, a long united filament two times the length of the floral bract, and dark anthers with bright yellow pollen.

Field growth characteristics: Determined through surveys of plants growing in the field in Tully, N.Y. and in Syracuse, N.Y.

Disease resistance: Displays a low incidence of rust disease; minor incidence of stem canker disease is occasionally evident.

Temperature tolerance: Stems typically do not suffer frost damage at temperatures as low as 10° F. and may suffer only minor tip dieback at lower temperatures.

Seed production: None — does not produce female flowers.

Biomass yield: Mean dry stem biomass yield produced through two growing seasons after coppice in eight 4-plant plots ('Oneida', 15.04 oven dry tons $ha^{-1}$ $yr^{-1}$) measured in a yield trial growing in Tully, N.Y. in February 2005 was 2.7-times greater than the mean stem biomass yield of one of its parents ('SX67', 5.52 oven dry tons $ha^{-1}$ $yr^{-1}$) and was more than 36% greater than two current production cultivars ('SV1', 11.04 oven dry tons $ha^{-1}$ $yr^{-1}$ and 'SX64', 10.35 oven dry tons $ha^{-1}$ $yr^{-1}$) growing in the same trial (FIG. 2.1).

What is claimed is:

1. A new and distinct variety of *Salix purpurea*×*S. miyabeana* plant, substantially as illustrated and described herein.

* * * * *

Fig. 1.1
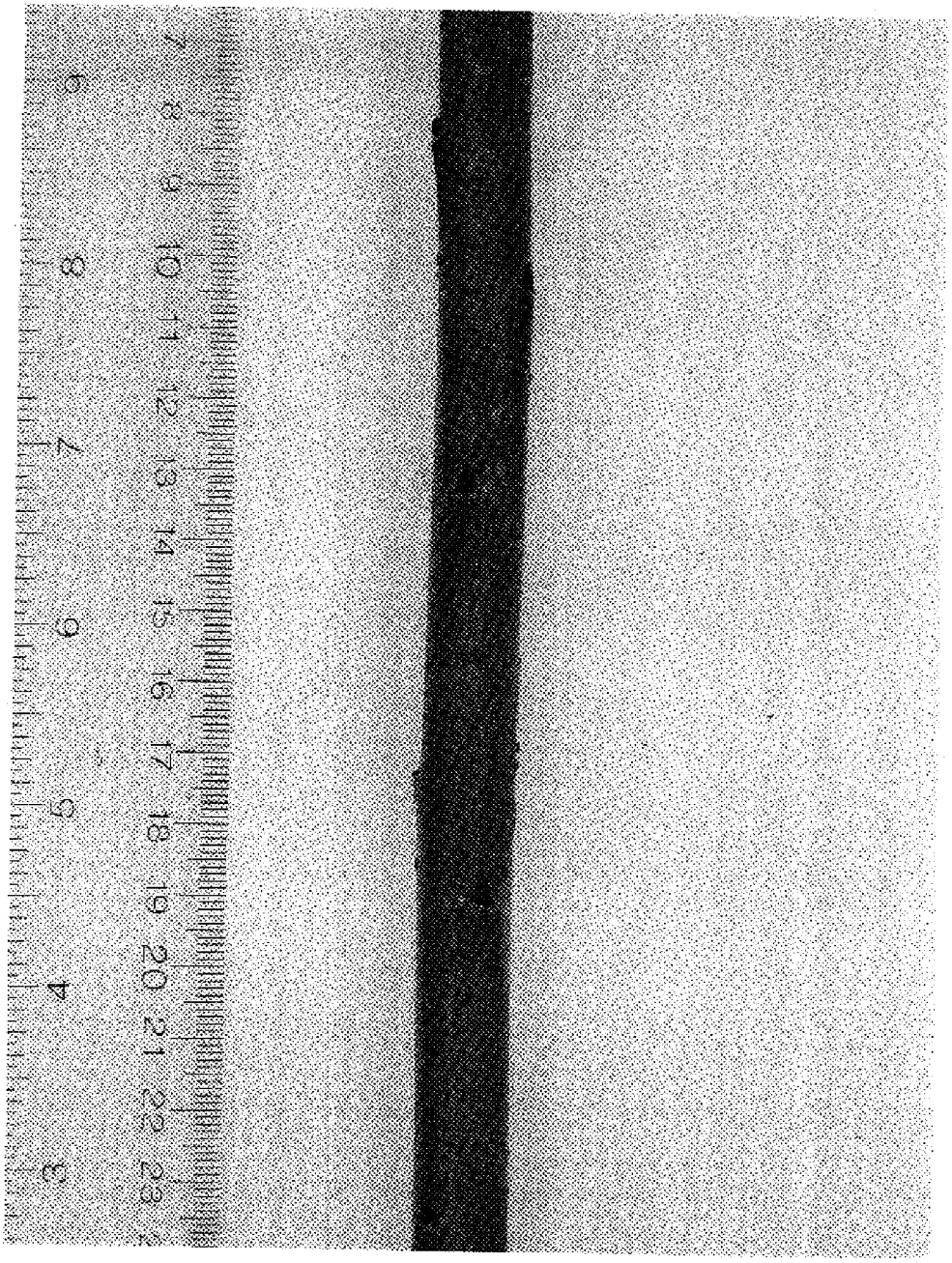

Fig. 1.2
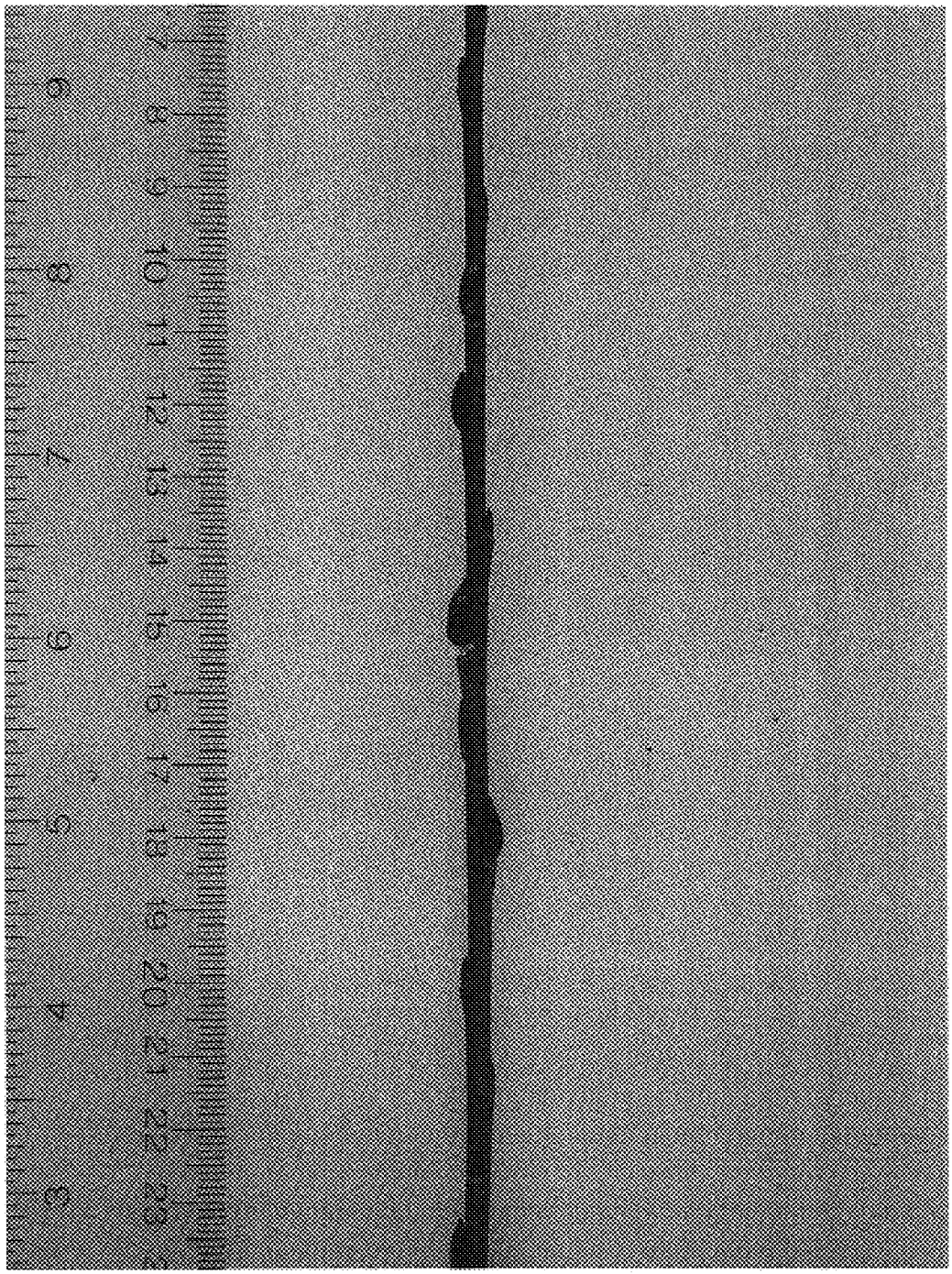

Fig. 1.3
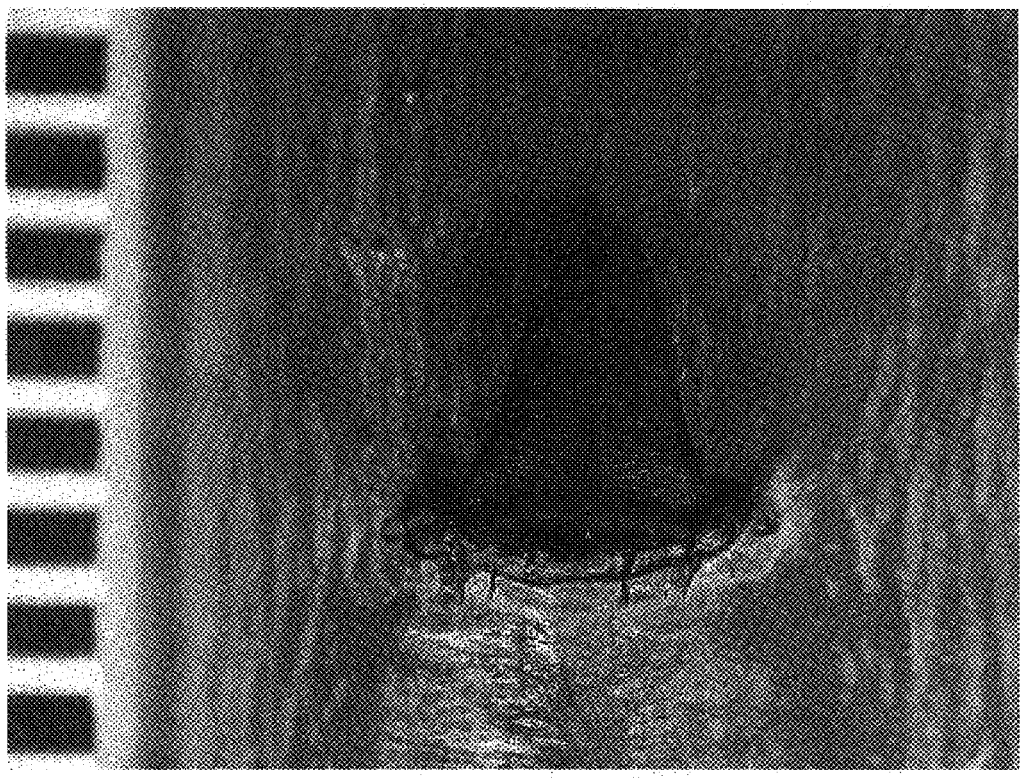

Fig. 1.4
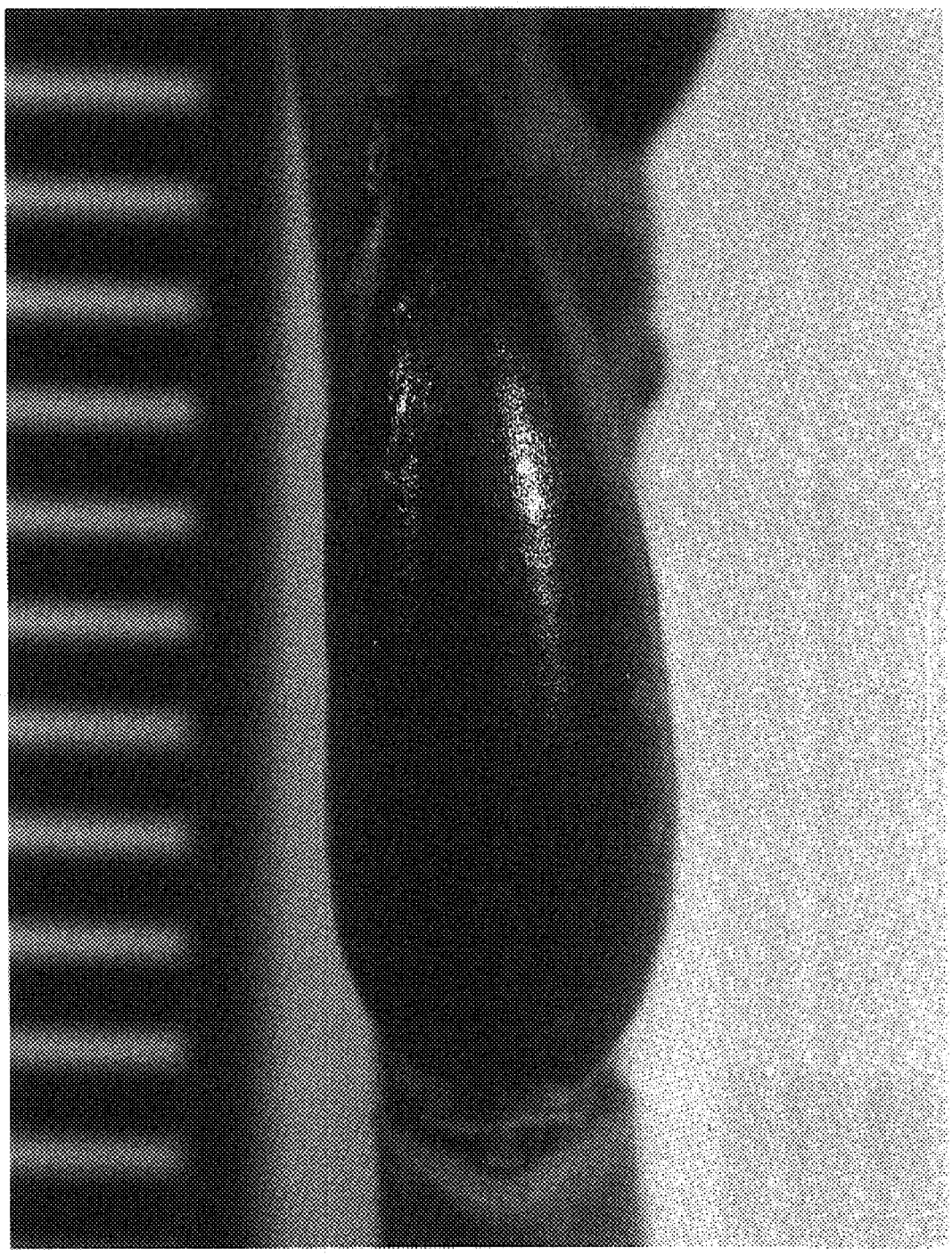

Fig. 1.5
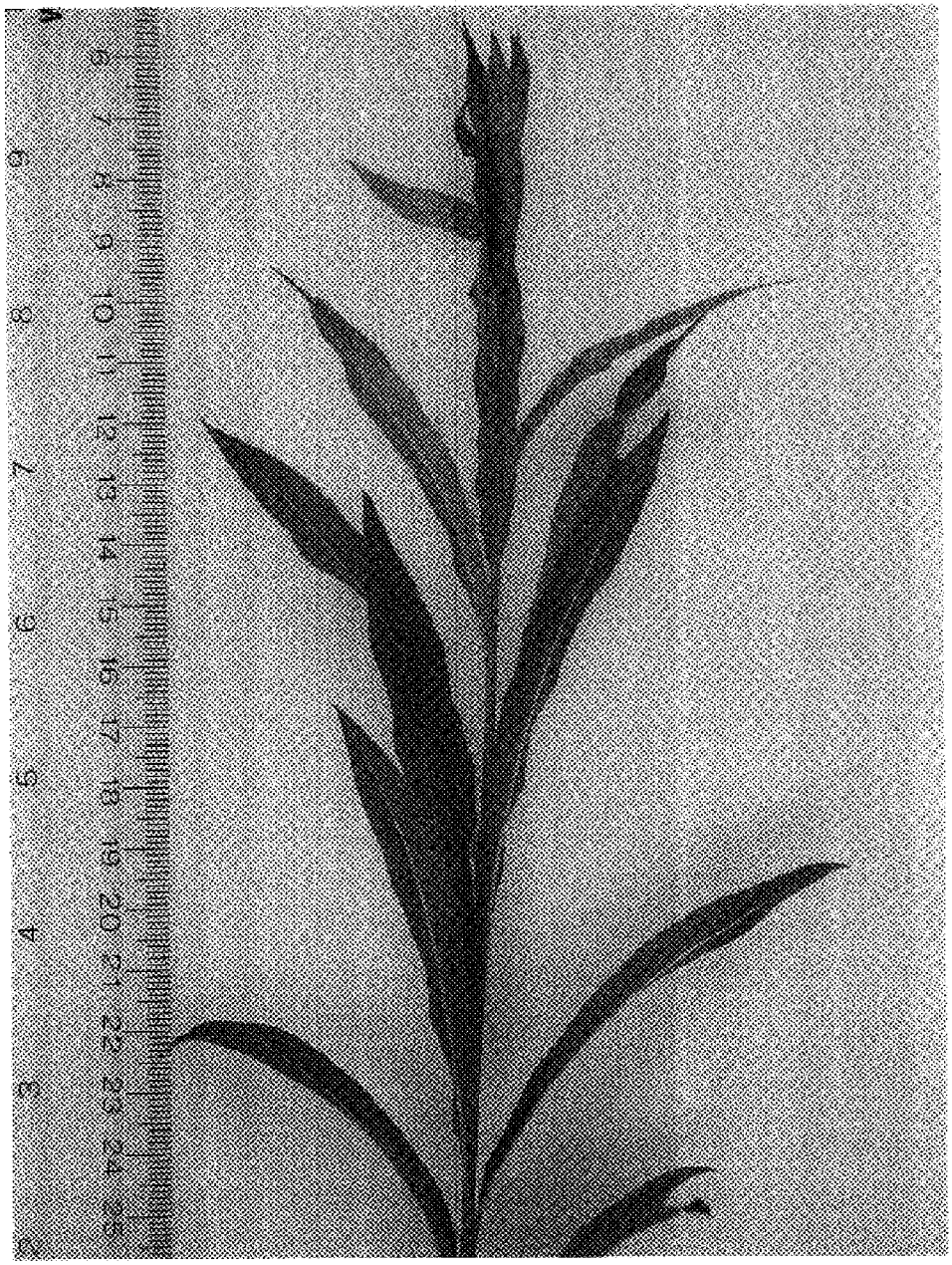

Fig. 1.6
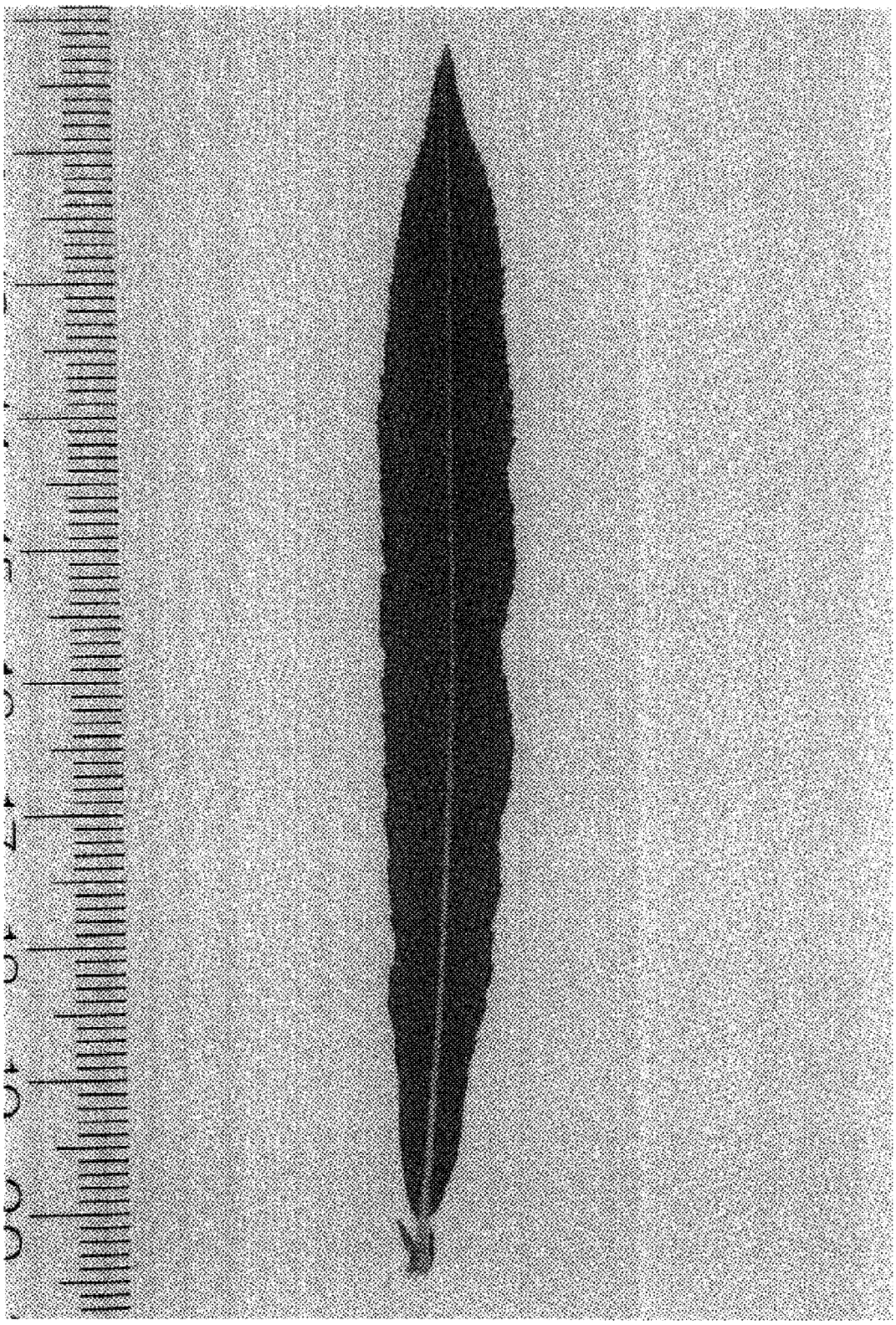

Fig. 1.7
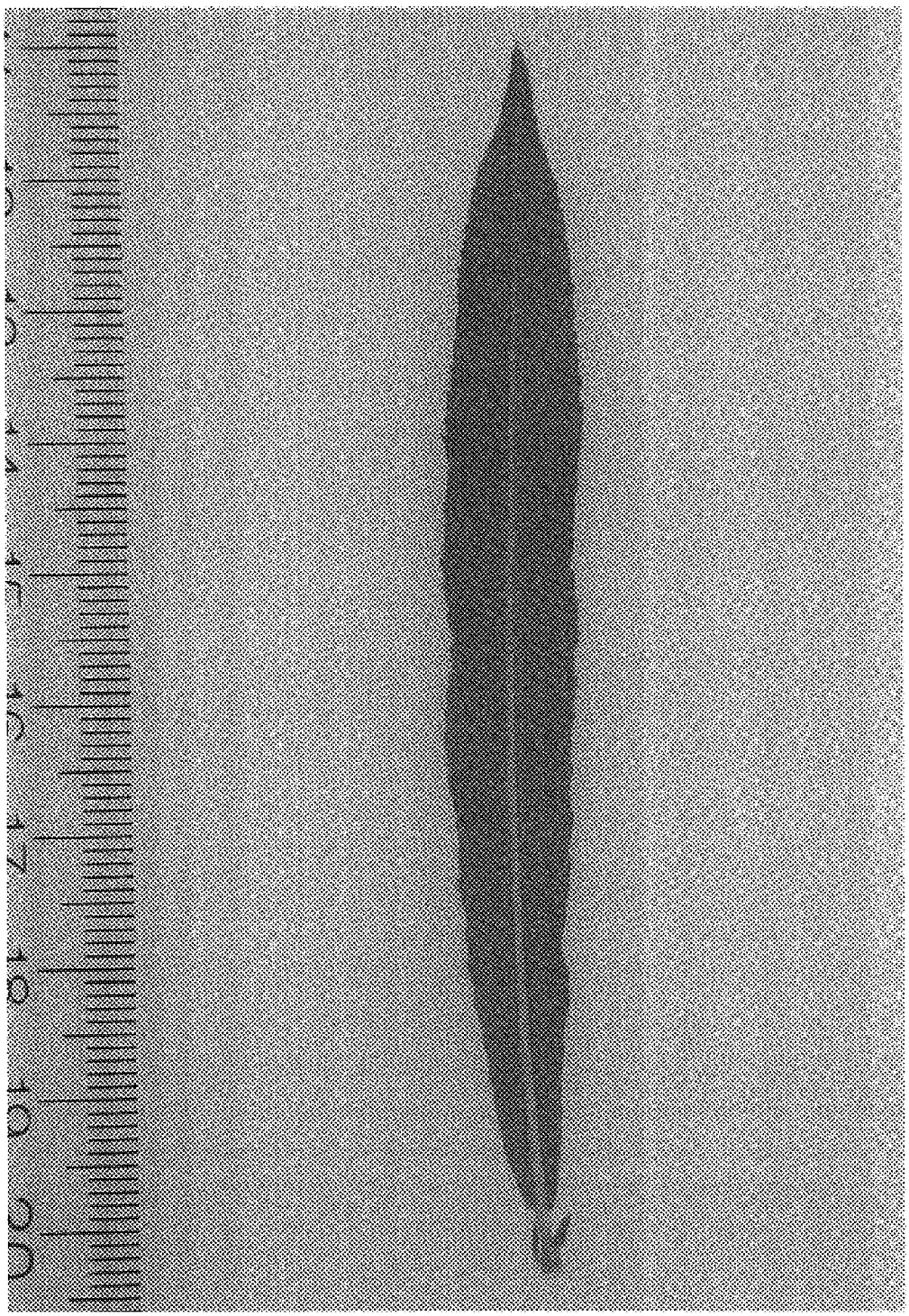

Fig. 1.8
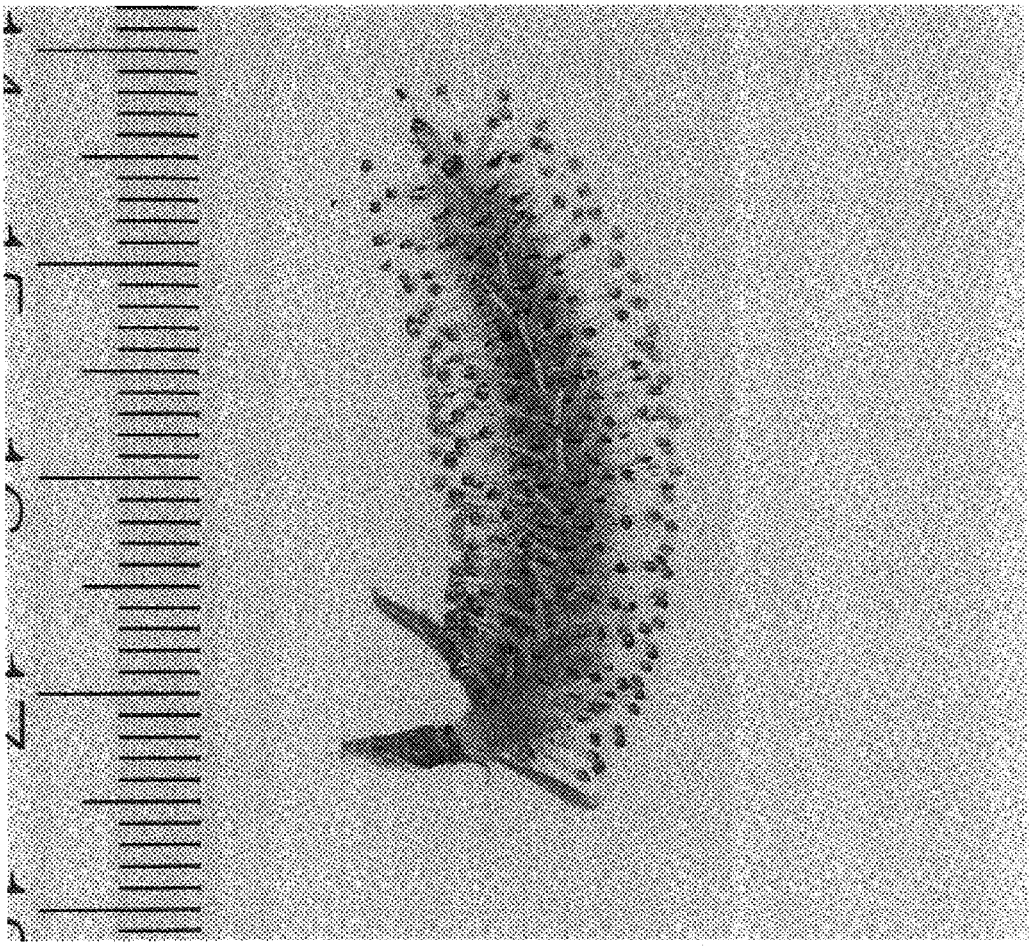

Fig. 1.9
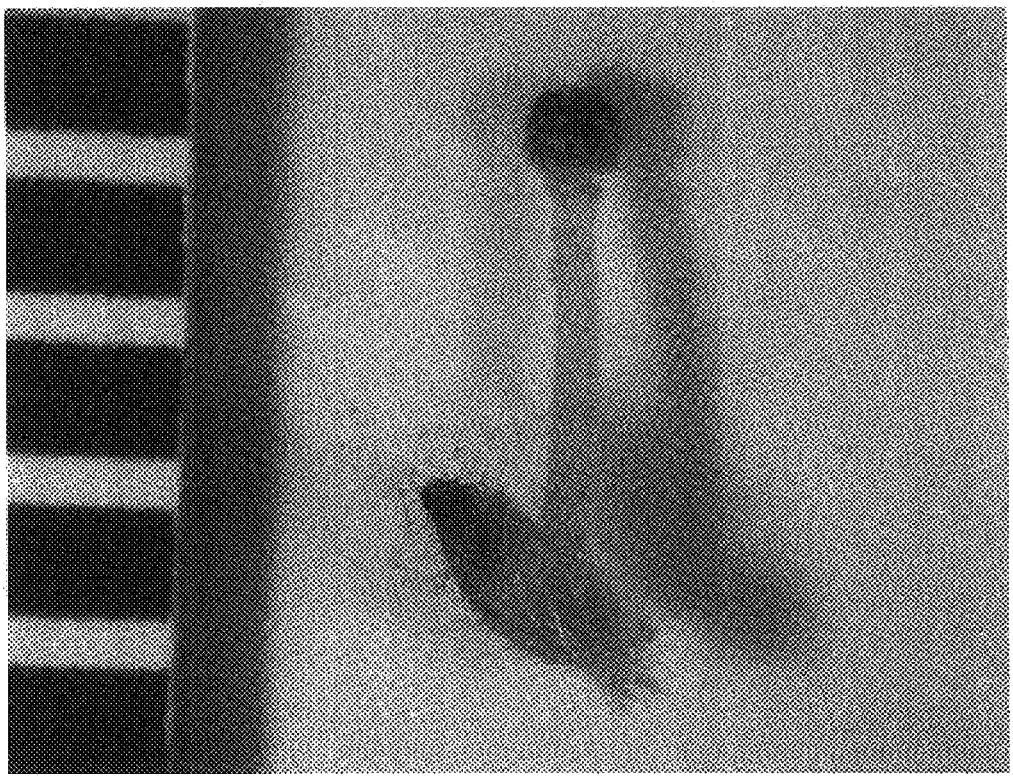

Fig. 1.10
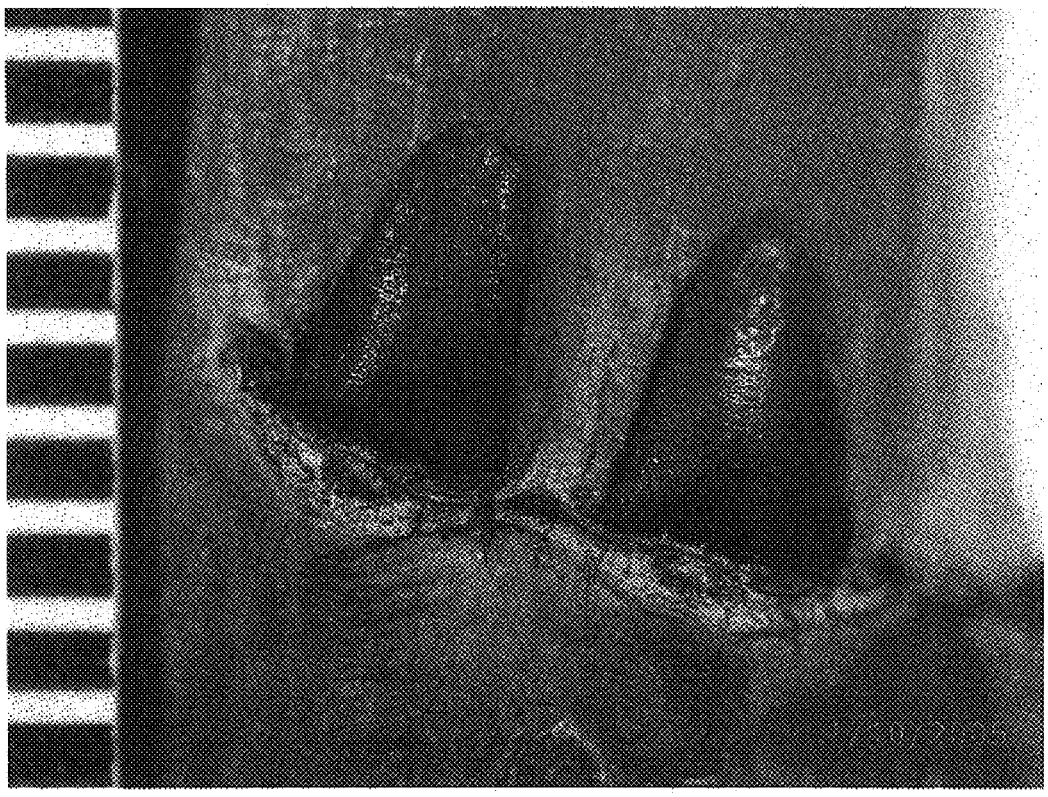

Fig. 2.1 - Biomass yield two years after coppice - Tully, NY
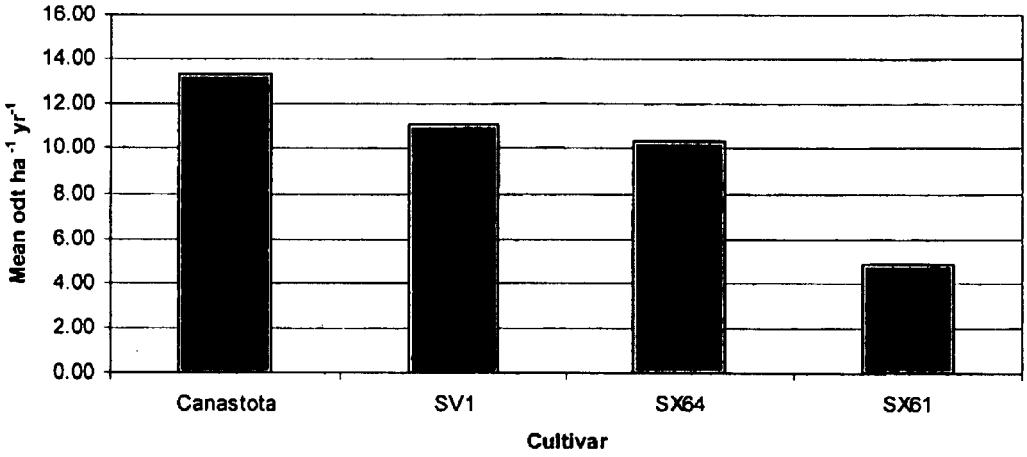

UNITED STATES PATENT AND TRADEMARK OFFICE

CERTIFICATE OF CORRECTION

PATENT NO. : PP 17,682 P2
APPLICATION NO. : 11/244975
DATED : May 1, 2007
INVENTOR(S) : Lawrence P. Abrahamson et al.

It is certified that error appears in the above-identified patent and that said Letters Patent is hereby corrected as shown below:

On Title Page, before the words "11 Drawing Sheets", insert -- 1 Claim --;

In the Cross Reference to Related Applications. Col. 1, Line 25. Delete "+1".

Signed and Sealed this

Third Day of July, 2007

JON W. DUDAS
*Director of the United States Patent and Trademark Office*